(12) United States Patent
Nichols et al.

(10) Patent No.: US 8,399,475 B2
(45) Date of Patent: Mar. 19, 2013

(54) CRYSTALLINE AND AMORPHOUS FORMS OF NALTREXONE HYDROCHLORIDE

(75) Inventors: Gary A. Nichols, Wildwood, MO (US); Michelle R. Menze, St. Louis, MO (US); Anthony Mannino, Maryland Heights, MO (US)

(73) Assignee: Mallinckrodt LLC, Hazelwood, MO (US)

( * ) Notice: Subject to any disclaimer, the term of this patent is extended or adjusted under 35 U.S.C. 154(b) by 596 days.

(21) Appl. No.: 12/595,543

(22) PCT Filed: Apr. 10, 2008

(86) PCT No.: PCT/US2008/004639
§ 371 (c)(1),
(2), (4) Date: Oct. 12, 2009

(87) PCT Pub. No.: WO2008/127618
PCT Pub. Date: Oct. 23, 2008

(65) Prior Publication Data
US 2010/0120814 A1 May 13, 2010

Related U.S. Application Data

(60) Provisional application No. 60/911,360, filed on Apr. 12, 2007.

(51) Int. Cl.
*A61K 31/485* (2006.01)
*C07D 489/08* (2006.01)
(52) U.S. Cl. .......................................... 514/282; 546/45
(58) Field of Classification Search .................. 514/282; 546/45
See application file for complete search history.

(56) References Cited

U.S. PATENT DOCUMENTS

| 3,332,950 A | 7/1967 | Blumberg et al. |
| 2005/0095279 A1 | 5/2005 | Gale et al. |

FOREIGN PATENT DOCUMENTS

WO  WO 2004/108084  12/2004

OTHER PUBLICATIONS

Le Dain et al., "Crystal Structure of Naltrexone Hydrochloride: Implications for Location of the Nicotinic Receptor Non-Competitive Inhibitor Binding Site", Aust. J. Chem., 1992, 45, pp. 635-640, XP 009102046.

*Primary Examiner* — Charanjit Aulakh

(57) ABSTRACT

The present invention relates to novel crystalline forms of naltrexone hydrochloride including hydrated and solvated forms and a novel amorphous form. The invention also describes methods of preparing the various crystalline forms. The present invention also relates to pharmaceutical compositions containing crystalline and amorphous forms of naltrexone hydrochloride, as well as methods of treating addictive behavior by administering the pharmaceutical compositions.

10 Claims, 12 Drawing Sheets

CRYSTALLINE AND AMORPHOUS FORMS OF NALTREXONE HYDROCHLORIDE

CROSS REFERENCE TO RELATED APPLICATIONS

This application is a national stage application of PCT/US2008/004639, filed Apr. 10, 2008, which claims the benefit of U.S. Provisional Application No. 60/911,360 filed Apr. 12, 2007.

FIELD OF THE INVENTION

The present invention relates to novel crystalline forms of naltrexone hydrochloride. The invention also encompasses related processes, compositions, and methods.

BACKGROUND OF THE INVENTION

Naltrexone hydrochloride is an opioid antagonist. The compound and methods for the synthesis of naltrexone are described in U.S. Pat. No. 3,332,950. Naltrexone hydrochloride (CAS: 16676-29-2) has the molecular formula $C_{20}H_{23}NO_4 \cdot HCl$ and the following structural formula:

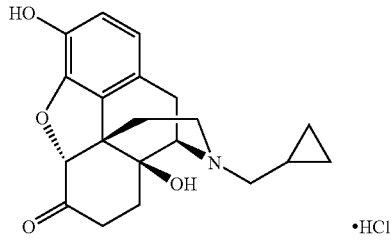 [SMILES: O=C1CC[C@@]2(O)[C@H]3Cc4ccc(O)c5c4[C@@]2(CCN3CC2CC2)[C@H]1O5 ; Cl]

Naltrexone hydrochloride is commercially available in tablet form (Revia®, Duramed) for the treatment of alcohol dependence and for the blockade of the effects of exogenously administered opioids, i.e. the maintenance of abstinence from opioids after opioid detoxification. A dosage of 50 mg Revia® purportedly blocks the pharmacological effects of 25 mg IV administered heroin for up to 24 hours.

There is a need for new crystalline forms of naltrexone hydrochloride. The discovery of new crystalline forms of a pharmaceutical compound provides an opportunity to improve the performance characteristics of a pharmaceutical product. It enlarges the repertoire of materials that a formulation scientist has available for designing, for example, a pharmaceutical dosage form of a drug with a targeted release profile or other desirable characteristic.

WO/04108084 discloses polymorph forms of naltrexone base, however, naltrexone base and naltrexone hydrochloride are different molecular species and therefore do not possess the same solid-state properties.

All documents cited herein, including the foregoing, are incorporated by reference in their entireties for all purposes.

SUMMARY OF THE INVENTION

The present invention is directed to crystalline forms and amorphous forms of naltrexone hydrochloride, as well as mixtures thereof.

A further aspect of the present invention is directed to methods for preparing crystalline forms and amorphous forms of naltrexone hydrochloride.

The present invention further pertains to the use of these crystalline forms of naltrexone hydrochloride in the treatment of an addictive disease, and to pharmaceutical formulations containing them.

Other novel features and advantages of the present invention will become more apparent to those skilled in the art upon examination of the following or upon learning by practice of the invention.

DETAILED DESCRIPTION OF THE INVENTION

Figure 1:
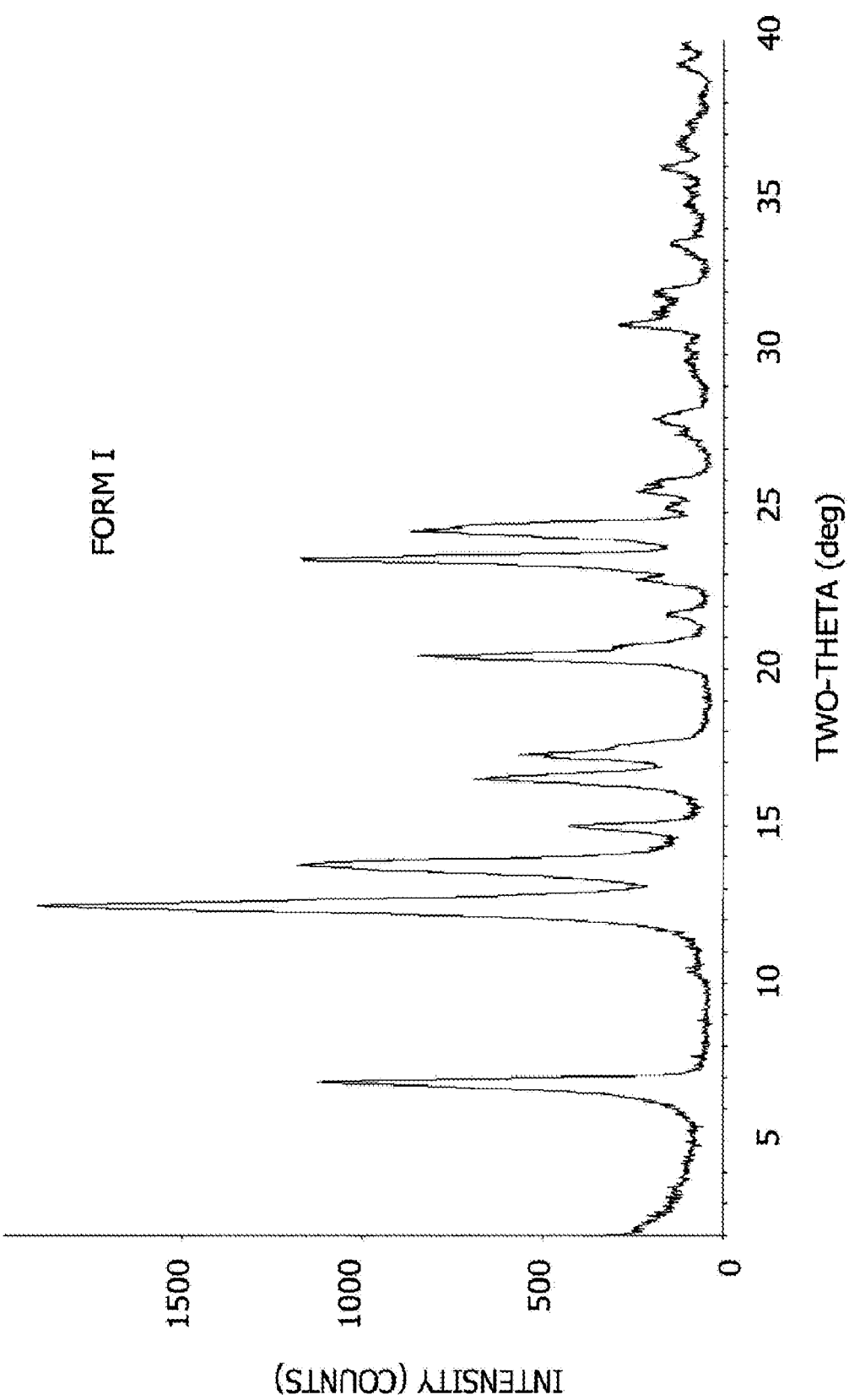
FIG. 1 shows the powder X-ray diffraction (pXRD) pattern for a prior art crystalline form of naltrexone hydrochloride—Form I.

The present invention describes several novel crystalline forms and an amorphous form of naltrexone hydrochloride and methods of making crystalline forms and an amorphous form of naltrexone hydrochloride.

Crystalline forms of naltrexone hydrochloride are made or transformed under different environmental conditions, such as exposure to heat or light, mechanical handling, interaction with excipients, or when placed in contact with water, organic solvents, mixtures of solvents, or vapor of solvents. Certain crystalline forms of naltrexone hydrochloride may be more stable in a given environmental condition or selected solvent system because each crystalline form may exhibit distinct physical and chemical properties. These properties include particle size, surface area, shape, flow characteristics, solubility, melting point, degree of hydration or solvation, and caking tendency. These properties may affect chemical processing, material handling, compatibility with excipients, segregation in a blend, dissolution rate of naltrexone hydrochloride in aqueous media, and stability of the final dosage form. Adverse effects may cause loss of production efficiency (time and cost), product quality and instability. Thus it is desirable to use a crystalline form of naltrexone hydrochloride with improved characteristics over other forms.

The methods used to produce novel crystalline forms from naltrexone hydrochloride are set forth below.

Preparation of Crystalline Forms of Naltrexone Hydrochloride

Crystalline forms of naltrexone hydrochloride may be prepared by the crystallization, precipitation, or slurry of naltrexone hydrochloride anhydrous (Mallinckrodt Inc.) out of a variety of solvent systems, including but not limited to methanol, isopropanol, ethanol, water, n-butanol, acetone, glacial acetic acid, ethyl acetate, methylene chloride, chloroform, acetonitrile, tetrahydrofuran (THF), hexane, toluene, dimethylsulfoxide (DMSO), ethyl ether, and mixtures thereof. In one embodiment, when two solvents are employed in the solvent system, the solvents may be present in a ratio from about 1:1 to about 1:100. In another embodiment, two solvent systems may be used: a first solvent system, in which naltrexone hydrochloride is particularly soluble, and a second solvent system, in which naltrexone hydrochloride is less soluble and typically more volatile than in the first solvent system.

Various methods of crystallization include but are not limited to slow evaporation, rapid evaporation, "hot" preparation, and slow diffusion. With these methods, the solvent may be evaporated off the solid naltrexone hydrochloride or solid naltrexone hydrochloride may be filtered from the residual solvent and dried. In one embodiment, the solid naltrexone hydrochloride is filtered using a fritted disc funnel and dried in a desiccator under vacuum.

In one embodiment, for slow evaporation experiments, each solvent system is saturated/near saturated with naltrexone hydrochloride in a small vial and set aside at room temperature and pressure to evaporate the solvent for an amount of time sufficient to induce crystallization of at least one crystalline form of naltrexone hydrochloride. In one embodiment, the amount of time sufficient to induce crystallization is from about 1 day to about 60 days. Following crystal growth, the solid material may be filtered from the residual solvent using a fritted disc funnel and dried in a desiccator under vacuum.

In another embodiment, rapid evaporation experiments are performed by saturating\near saturating a solvent system with naltrexone hydrochloride and then quickly roto-evaporating off the solvent.

In yet another embodiment, described as "hot" preparation, an aliquot of each solvent system is heated to boiling/near boiling. Naltrexone hydrochloride is then added slowly until the solvent is saturated/near saturated. The solution is then cooled to induce crystallization of at least one crystalline form of naltrexone hydrochloride. In one embodiment, the solution is cooled at room temperature for an amount of time sufficient to induce crystallization. In another embodiment, the solution is cooled by placing the solution in an ice bath to induce crystallization. Following crystal growth, the solid material may be filtered from the residual solvent using a fritted disc funnel and dried in a desiccator under vacuum.

In an alternative approach to the "hot" preparation embodiment noted above, naltrexone hydrochloride (e.g., anhydrous naltrexone hydrochloride) is mixed with a solvent system (e.g., water) and heated to aid dissolution to a temperature, for example, of about 40° C., about 50° C., about 60° C. or more. Hydrochloric acid (e.g., concentrated hydrochloric acid) is added, and the solution is cooled (e.g., to room temperature or below, such as for example to a temperature of less than about 20° C., about 10° C., or even about 5° C.). The addition of the common ion from the hydrochloric acid, coupled with the reduced temperature, results in the crystallization of the naltrexone hydrochloride (see, e.g., Form XI).

In yet another embodiment, slow diffusion experiments are performed by dissolving naltrexone hydrochloride in a first solvent system, in which the naltrexone hydrochloride is soluble, in a small vial and then placing the small vial in a sealed larger flask that contains a second solvent system, in which naltrexone hydrochloride is less soluble and is typically more volatile than the first solvent system. In one embodiment, the first solvent system is either ethanol or methanol and the second solvent system is ethyl acetate, hexane, chloroform, or ethyl ether. The flask is set aside for an amount of time sufficient to allow for vapor equilibration and crystallization of the naltrexone hydrochloride. Following crystal growth, the solid material may be filtered from the residual solvent using a fritted disc funnel and dried in a desiccator under vacuum.

For slurry preparations, a solvent system is saturated with naltrexone hydrochloride in a flask or similar container to which additional solid naltrexone hydrochloride is added. The resulting slurry is then stirred for an amount of time sufficient to convert a first crystalline form of naltrexone hydrochloride to a second crystalline form of naltrexone hydrochloride, using for example, a magnetic stir-bar. In a preferred embodiment, the slurry is stirred for preferably 10 to 20 days, more preferably, 13 to 17 days, most preferably 13, 15 or 17 days. The second crystalline form of naltrexone hydrochloride may then be filtered from the residual solvent, for example, with a fritted disc funnel.

Precipitation preparations may be completed by first dissolving naltrexone hydrochloride in a first solvent system in which naltrexone hydrochloride is particularly soluble and then adding a second solvent system, in which naltrexone hydrochloride is less soluble, slowly to precipitate the naltrexone hydrochloride from solution.

The prepared crystalline forms and amorphous form of naltrexone hydrochloride were subsequently characterized by powder X-ray diffraction ("pXRD") analysis.

pXRD analysis was conducted using a Siemens D500 X-ray Diffractometer. All samples were unground, uniformly crushed with a spatula edge, and placed on a quartz, zero background holder. The following instrument parameters were utilized: Scan range: 2.0 to 40.0° 2θ, Step size: 0.02° 2θ, Scan time per step: 1.0 seconds, Radiation source: copper Kα (1.5406 Å), X-ray tube power: 40 kV/30 mA. Those skilled in the art of X-ray crystallography will appreciate that peak positions determined on different instruments may vary by as much as +0.2 degrees.

Each crystalline form and amorphous form of naltrexone hydrochloride exhibited a distinctly different pXRD pattern as set forth in FIGS. 1 to 12 and Table 1.

TABLE 1

CRYSTALLINE NALTREXONE HYDROCHLORIDE XRPD PEAK (°2Θ) AND RELATIVE INTENSITIES

| Form I | | Form II | | Form III | | Form IV | | Form V | |
|---|---|---|---|---|---|---|---|---|---|
| °2θ | Ht I % | °2θ | Ht I % | °2θ | Ht I % | °2θ | Ht I % | °2θ | Ht I % |
| 6.9* | 59.9 | 8.0* | 60.6 | 7.7* | 100.0 | 6.1* | 100.0 | 7.4* | 100.0 |
| 12.5* | 100.0 | 9.2 | 10.2 | 8.2 | 8.8 | 10.8* | 28.3 | 9.5 | 13.2 |
| 13.8* | 55.0 | 10.8* | 48.2 | 9.9* | 44.4 | 12.2* | 31.3 | 11.1* | 59.5 |
| 15.0* | 17.4 | 11.7* | 100.0 | 11.6* | 28.3 | 13.7* | 28.3 | 12.0* | 77.6 |

TABLE 1-continued

CRYSTALLINE NALTREXONE HYDROCHLORIDE XRPD PEAK (°2Θ) AND RELATIVE INTENSITIES

| °2θ | Ht I % | °2θ | Ht I % | °2θ | Ht I % | °2θ | Ht I % | °2θ | Ht I % |
|---|---|---|---|---|---|---|---|---|---|
| 16.5* | 34.3 | 12.3 | 7.5 | 12.1* | 30.1 | 14.0 | 10.0 | 12.4 | 17.9 |
| 17.3* | 29.0 | 12.9* | 30.1 | 12.4* | 55.6 | 15.5* | 22.7 | 13.3* | 38.6 |
| 17.6* | 13.9 | 14.4 | 9.0 | 13.4* | 23.7 | 16.5* | 15.7 | 14.9* | 38.9 |
| 20.4* | 44.4 | 14.7 | 5.1 | 14.9 | 9.3 | 17.6 | 10.8 | 15.4 | 7.1 |
| 21.8 | 5.6 | 15.5 | 7.3 | 15.5 | 9.1 | 18.3 | 8.6 | 15.6* | 47.1 |
| 22.9 | 10.4 | 15.9* | 33.1 | 16.0* | 27.3 | 21.4* | 19.5 | 16.6* | 19.3 |
| 23.6* | 61.6 | 16.6 | 5.7 | 16.9 | 9.9 | 21.7 | 8.6 | 18.6 | 7.7 |
| 24.5* | 38.3 | 17.1* | 27.9 | 20.0* | 11.7 | 23.0 | 9.5 | 19.0* | 25.7 |
| 25.7 | 11.1 | 18.5* | 15.7 | 23.4* | 24.6 | 23.6* | 20.6 | 21.0 | 7.5 |
| 28.0 | 7.9 | 20.8* | 14.2 | 25.7 | 8.6 | 24.0 | 6.1 | 21.4 | 17.9 |
| 31.0 | 12.2 | 22.1 | 5.8 | 26.8* | 11.4 | 24.5* | 21.0 | 22.1 | 11.4 |
| 31.4 | 7.2 | 23.0 | 10.2 | 32.3 | 4.8 | 24.7* | 12.6 | 22.9* | 28.9 |
| 32.0 | 8.0 | 23.5* | 23.4 | | | 29.1 | 6.0 | 23.4* | 18.7 |
| 33.5 | 5.0 | 25.3 | 8.7 | | | 29.8 | 6.0 | 24.1 | 14.6 |
| 36.0 | 5.6 | 25.7 | 11.6 | | | 31.2 | 5.6 | 25.0* | 15.7 |
| | | 25.9 | 11.5 | | | | | 26.0 | 8.8 |
| | | 26.4* | 20.3 | | | | | 26.3 | 6.4 |
| | | 27.5 | 7.1 | | | | | 26.8 | 11.9 |
| | | 28.4 | 5.3 | | | | | 27.0 | 13.6 |
| | | 31.3 | 7.2 | | | | | 28.1 | 6.5 |
| | | 32.8 | 5.8 | | | | | 29.4 | 6.3 |
| | | 33.4 | 4.1 | | | | | 30.8 | 10.0 |
| | | | | | | | | 32.5 | 7.5 |
| | | | | | | | | 33.0 | 6.7 |
| | | | | | | | | 37.0 | 9.1 |
| | | | | | | | | 42.7 | 6.0 |

| Form VI | | Form VII | | Form VIII | | Form IX | | Form X | | Form XI | |
|---|---|---|---|---|---|---|---|---|---|---|---|
| °2θ | Ht I % | °2θ | Ht I % | °2θ | Ht I % | °2θ | Ht I % | °2θ | Ht I % | °2θ | Ht I % |
| 7.4* | 100.0 | 7.4* | 52.0 | 8.1 | 6.7 | 10.2 | 3.6 | 7.4* | 56.6 | 8.3* | 70.5 |
| 9.8* | 20.3 | 10.1* | 26.4 | 11.4* | 19.3 | 11.5 | 8.8 | 9.4 | 5.2 | 11.5* | 93.8 |
| 11.1* | 25.0 | 11.5* | 100.0 | 11.8* | 100.0 | 11.9* | 27.9 | 11.0* | 83.2 | 11.9* | 80.4 |
| 12.1* | 24.5 | 12.2* | 61.4 | 12.7 | 10.4 | 12.2* | 100.0 | 12.1* | 100.0 | 12.9 | 32.6 |
| 12.7 | 5.9 | 13.2* | 87.3 | 13.1* | 42.1 | 13.2* | 51.6 | 12.6* | 25.1 | 16.5* | 100.0 |
| 13.6 | 9.7 | 14.9* | 38.3 | 13.5* | 36.5 | 14.8* | 47.0 | 13.4* | 42.8 | 17.2* | 36.8 |
| 14.8 | 7.0 | 15.9* | 73.1 | 15.9* | 20.5 | 15.4* | 43.7 | 14.9* | 27.4 | 18.1 | 4.5 |
| 15.7 | 9.7 | 16.2* | 55.6 | 16.3 | 6.2 | 15.9* | 52.8 | 15.7* | 40.7 | 18.7 | 1.9 |
| 16.7* | 25.7 | 19.5 | 12.1 | 17.7 | 11.9 | 16.5* | 69.0 | 16.8* | 21.6 | 20.1 | 5.0 |
| 18.7 | 11.6 | 20.3* | 30.6 | 19.3 | 13.6 | 18.8* | 28.5 | 18.9* | 21.9 | 20.6 | 15.1 |
| 19.4 | 6.3 | 21.0 | 5.3 | 19.6* | 14.5 | 19.6 | 9.6 | 21.2 | 2.4 | 21.2 | 11.8 |
| 20.3* | 26.1 | 21.7 | 14.1 | 21.6 | 12.3 | 20.5* | 35.6 | 21.4 | 5.3 | 21.9* | 42.8 |
| 22.6 | 5.9 | 21.9* | 52.3 | 22.6* | 18.8 | 21.0 | 8.2 | 21.9 | 2.2 | 22.9 | 2.5 |
| 23.4* | 23.1 | 22.6* | 25.9 | 23.1* | 20.7 | 21.5 | 7.3 | 22.4* | 14.8 | 23.8* | 36.4 |
| 25.1* | 20.3 | 23.2 | 10.3 | 23.8 | 13.5 | 22.0* | 38.7 | 22.9 | 5.9 | 24.1 | 18.7 |
| 25.4 | 12.2 | 24.9 | 18.2 | 24.5* | 25.6 | 22.9* | 53.9 | 23.2 | 13.9 | 24.5 | 15.8 |
| 25.9 | 8.2 | 25.6 | 12.0 | 25.4 | 7.1 | 23.6 | 13.4 | 23.7* | 34.9 | 24.8 | 17.6 |
| 27.4* | 16.8 | 26.6* | 23.2 | 25.8* | 25.4 | 23.9* | 78.9 | 24.3* | 12.2 | 25.9 | 19.9 |
| 27.8* | 16.6 | 27.4 | 6.4 | 26.1 | 7.7 | 24.6 | 10.8 | 24.8 | 8.1 | 26.4 | 9.6 |
| 28.5 | 6.1 | 27.9 | 10.2 | 26.7 | 5.7 | 25.0 | 10.2 | 25.1 | 5.1 | 26.9 | 26.9 |
| 29.4 | 5.8 | 28.3 | 6.8 | 28.5 | 9.9 | 25.6* | 23.7 | 25.7 | 7.5 | 28.2 | 6.1 |
| 30.2 | 6.8 | 28.9 | 5.2 | 29.9 | 7.2 | 26.0 | 9.0 | 26.2 | 6.8 | 28.8 | 3.9 |
| 32.2 | 11.4 | 31.1 | 6.6 | 30.2 | 11.5 | 26.5* | 61.8 | 27.0* | 10.4 | 29.5 | 10.1 |
| 33.8 | 9.1 | 34.0 | 5.6 | 31.0 | 9.3 | 27.5 | 7.7 | 35.7 | 3.3 | 30.4 | 6.0 |
| 37.9 | 6.2 | | | 32.1 | 11.5 | 27.9 | 17.5 | | | 31.0 | 5.4 |
| 41.6 | 14.6 | | | 33.4 | 5.5 | 28.2* | 16.1 | | | 31.6 | 11.2 |
| | | | | 34.7 | 8.6 | 29.0 | 7.5 | | | 32.0 | 4.6 |
| | | | | 36.8 | 9.1 | 29.6 | 7.1 | | | 32.5 | 10.9 |
| | | | | | | 29.9 | 9.8 | | | 33.3 | 5.0 |
| | | | | | | 30.3 | 11.7 | | | 33.6 | 3.5 |
| | | | | | | 31.3* | 25.1 | | | 34.7 | 3.9 |
| | | | | | | 32.1 | 19.8 | | | 35.9 | 4.2 |
| | | | | | | 32.6 | 12.2 | | | 36.5 | 7.9 |
| | | | | | | 33.0 | 17.2 | | | 37.9 | 11.0 |
| | | | | | | 33.5 | 11.0 | | | 39.6 | 4.3 |
| | | | | | | 34.2 | 11.5 | | | | |
| | | | | | | 36.5 | 7.1 | | | | |
| | | | | | | 36.7 | 10.9 | | | | |
| | | | | | | 37.4 | 6.2 | | | | |
| | | | | | | 38.0 | 13.7 | | | | |
| | | | | | | 39.8 | 8.3 | | | | |
| | | | | | | 40.6 | 9.7 | | | | |
| | | | | | | 41.6 | 7.4 | | | | |
| | | | | | | 42.0 | 8.1 | | | | |
| | | | | | | 42.7 | 6.1 | | | | |

A crystalline naltrexone hydrochloride form having at least four of the peaks indicated by an asterisk (+/−0.2 deg 2θ) within one form of Table 1 are preferred embodiments of the invention. More preferable is a form having at least eight of the peaks that are indicated by an asterisk (+/−0.2 deg 2θ). Even more preferable is a form having at least ten of the peaks that are indicated by an asterisk (+/−0.2 deg 2θ). Even more preferable is a form having all of the peaks that are indicated in Table 1 for that particular form (+/−0.2 deg 2θ).

Commercially available naltrexone hydrochloride anhydrous (Mallinckrodt) was found to be Form I. Further, Form VI, naltrexone hydrochloride tetrahydrate, has been reported in the literature (A. C. Le Dain, et al. (1992) Aust. J. Chem., 45, 635.). The present invention describes novel forms obtained and characterized including naltrexone hydrochloride Forms II, III, IV, V, VII, VIII, IX, X and XI, as well as amorphous naltrexone hydrochloride. The novel crystalline forms include three solvated forms (Forms III, IV, and V), two chloroform solvates (Forms VII, XI), an ethyl acetate solvate (Form X) and three hydrated polymorphs (Forms II, VIII and XI).

Crystalline Form II was identified as a hydrated species, which incorporated as much as 2 moles of water per mole of naltrexone hydrochloride. The water content of samples present as crystalline Form II was observed to vary from as low as 1-2% to as high as 8-9%. Other crystalline forms were observed to convert to this Form II of naltrexone hydrochloride when exposed to high humidity.

Form III was revealed to be a solvated crystalline form. This form may contain bound Isopropanol.

Form IV was isolated as a methanol solvate. In addition to methanol, this crystalline form was also observed to incorporate ethanol and ethyl ether.

Form V was first isolated as an acetone solvate. This crystalline form was also observed to incorporate DMSO and n-butanol.

Form VII was identified as a chloroform solvate.

Form VIII was discovered to be a hydrated species, which contained about 8% water by mass.

Form IX was identified as a second chloroform solvate.

Form X was isolated as an ethyl acetate solvate.

Form XI was discovered to be a hydrated species (such forms have been observed to typically contain between about 2% and about 3% water, by mass).

Amorphous naltrexone hydrochloride displayed an x-ray diffraction pattern with broad, non-distinct peaks.

The present invention also includes mixtures of the forms described herein. Thus, the invention includes, for example, naltrexone hydrochloride Form II alone or in combination with one or more of the other forms described herein. Such combinations can include compositions that have between 1 and 100% by weight of any particular form. Preferred amounts of one naltrexone hydrochloride form include at least about 10% by weight of the total crystalline product, preferably at least about 20%, at least about 30%, at least about 40%, at least about 50%, at least about 60%, at least about 70%, at least about 80%, or at least about 90% by weight of total crystallinity. The percentages represent the fraction of crystallinity as determined by relative peak intensity of characterizing peaks.

The crystalline forms of the invention and the compositions containing them have the advantage that they are in a form which provides for beneficial properties. For example, hydrated naltrexone hydrochloride Forms II and VIII are more stable under wet and/or high humidity environments than non-hydrated forms. Therefore, if during formulation, naltrexone hydrochloride is wet granulated or dissolved in water and spray dried, a conversion to a hydrated form could potentially occur if the starting material was not a hydrated form of naltrexone hydrochloride. Further, depending upon the intended use, the novel naltrexone hydrochloride forms may have improved chemical and solid state stability. For example, they may be stable when stored over prolonged periods of time. They may be prepared in good yields, in higher purity, in less time, more conveniently and at a lower cost, than forms of naltrexone hydrochloride prepared previously.

In accordance with the present invention, these novel crystalline forms of naltrexone hydrochloride may be prepared as pharmaceutical compositions that are particularly useful for the treatment of a patient afflicted with addictive diseases or central nervous system disorders wherein such disease states may be treated by the administration of an effective amount of naltrexone hydrochloride of the present invention to a patient in need thereof. Such compositions can be manufactured utilizing techniques known in the art and comprise a therapeutically effective amount of at least one new crystalline form or an amorphous form of naltrexone hydrochloride with pharmaceutically acceptable carriers, excipients and/or diluents that are known to those skilled in the art.

Naltrexone hydrochloride crystalline forms or amorphous naltrexone hydrochloride are administered to a person in a therapeutically effective amount, i.e. an amount effective to treat addictive behavior, including alcohol or opioid dependence and eating disorders. The therapeutically effective amount of naltrexone hydrochloride crystalline form necessary to treat addictive behavior is dependent upon the patient (size, age, health, and response, e.g.), the severity and extent of addiction, the particular crystalline form employed, the method of administration, the bioavailability characteristic of the formulation administered, the dosing regimen, and other relevant circumstances. As used herein, the term "patient" refers to a warm blooded animal, including but not limited to humans, such as a mammal which is afflicted with a particular disease state.

Administration of pharmaceutical compositions including naltrexone hydrochloride crystalline forms alone or in conjunction with other compounds can be local or systemic, or a combination of therapies. Systemic administration is preferred in some embodiments. Systemic administration can be via any method known in the art such as, for example, oral administration of lozenges, tablets, capsules, sub-lingual tablets, syrups, suspensions, granules, or other edible compositions; intravenous, intramuscular, or intradermal administration, e.g., by suspension, sterile injections, including depot versions; implants; parenteral administration of fluids and the like. In one embodiment, the novel naltrexone hydrochloride forms of this invention can be tabletted with conventional tablet bases such as lactose, sucrose, and cornstarch in combination with binders, such as microcrystalline cellulose, crospovidone, acacia, cornstarch, or gelatin, disintegrating agents such as potato starch or alginic acid, a lubricant such as hydroxypropyl methylcellulose, stearic acid or magnesium stearate, flavoring agents or coloring agents, such as yellow iron oxide and red iron oxide, and other excipients such as colloidal silicon dioxide, titanium dioxide, polyethylene glycol, and polysorbate 80. For parenteral administration the novel naltrexone hydrochloride forms may be dissolved in a physiologically acceptable pharmaceutical carrier and administered as either a solution or a suspension. Illustrative of suitable pharmaceutical carriers include water, saline, dextrose solutions, fructose solutions, ethanol, or oils of animal, vegetative, or synthetic origin. The pharmaceutical carrier may also contain preservatives and buffers as are known in the art.

For local administration, the novel naltrexone hydrochloride forms of the present invention may be topically applied to the skin or mucosa in association with a pharmaceutically acceptable carrier in which the naltrexone hydrochloride is dispersed or solubilized. Carriers may be aqueous compositions, lotions, creams, ointments, soaps, sustained release preparations such as patches and the like.

In one embodiment of the present invention, a naltrexone hydrochloride crystalline form is taken orally as a tablet. Typical doses vary from about 12.5 mg to about 150 mg, and in preferred embodiments from about 25 mg to about 100 mg. In other embodiments, typical doses are 25 mg, 50 mg, or 100 mg. In still other embodiments, smaller doses such as up to 12.5 mg, more narrowly up to 1 mg are employed. In another embodiment, a naltrexone hydrochloride crystalline form is administered intravenously as a sterile injection. Other preferred amounts and modes of administration are able to be determined by one skilled in the art using formulation technology known in the art, described for example in Remington's Pharmaceutical Sciences, latest edition, Mack Publishing Co.

In one embodiment, a dosing regimen includes administering to a patient in need 50 mg of the naltrexone hydrochloride crystalline form every 24 hours. In other embodiments, the patient is administered 50 mg of naltrexone hydrochloride crystalline form every weekday with 100 mg on Saturday, 100 mg every other day, or 150 mg every third day.

Examples

Naltrexone hydrochloride samples were prepared as described in Table 2 and the crystalline character of the naltrexone hydrochloride was demonstrated by pXRD analysis (FIGS. 2-5 and 7-12).

TABLE 2

| FORM | DESCRIPTION | PREPARATION |
|---|---|---|
| II | Hydrated - contains bound water (~1.0-9.0% by mass) | Obtained by slow evaporation from ethanol/methanol, methanol/acetonitrile, methanol/THF, methanol/hexane or methanol/toluene mixtures open to the atmosphere.<br>Obtained by hot preparation of naltrexone hydrochloride in methanol/water mixture or water/isopropanol mixture.<br>Obtained by slurrying naltrexone hydrochloride in water for 13 days.<br>Obtained by exposing Form I to humidities above 70% RH. |
| III | Solvated - May contain bound isopropyl alcohol. | Obtained by slow evaporation from n-butanol/methanol mixture or methanol/isopropanol mixture.<br>Obtained by hot preparation/slow evaporation from glacial acetic acid/water mixture.<br>Obtained by slurrying naltrexone hydrochloride in isopropanol for 17 days. |
| IV | Solvated - May contain bound methanol, ethanol and ethyl ether. | Obtained by slow diffusion from methanol/ethyl acetate mixture, ethanol/ethyl ether mixture, or methanol/ethyl ether. |
| V | Acetone Solvate - May contain bound DMSO and n-butanol. | Obtained by hot preparation of naltrexone hydrochloride in methanol/acetone mixture.<br>Obtained by hot preparation of naltrexone hydrochloride in DMSO followed by ice cooling.<br>Obtained by slurrying naltrexone hydrochloride in acetone for 15 days.<br>Obtained by slurrying naltrexone hydrochloride in n-butanol for 13 days. |
| VII | Chloroform Solvate | Obtained by slow evaporation from 74:1 ratio chloroform/methanol. |
| VIII | Hydrated - contains bound water (~8.0% by mass) | Obtained by hot preparation of naltrexone hydrochloride in acetonitrile/water mixture. |
| IX | Chloroform Solvate | Obtained by slow diffusion in methanol/chloroform. |
| X | Ethyl Acetate Solvate | Obtained by slow evaporation from ethyl acetate. |
| XI | Hydrated - contains bound water (~2-3% by mass) | Obtained by hot preparation of naltrexone hydrochloride in water/concentrated HCl mixture. |
| Amorphous | | Obtained by rapid evaporation from methanol.<br>Obtained by hot preparation of naltrexone hydrochloride in water/ethanol mixture. |

Referring specifically to Form XI, it is to be noted that this sample was prepared as follows: to a round bottom flask was added 35 g of anhydrous naltrexone HCl and 150 ml of water. This mixture was heated to 60° C. and to it was added 35 ml of concentrated hydrochloric acid. The solution was cooled to between 5 and 10° C. over 2 hours to cause crystallization to occur. The crystallizing slurry was stirred for 1 hour and then the crystallized naltrexone HCl was filtered and washed with 30 ml of cold water (between 0-5° C.). The wet filter cake was collected and dried in a forced air oven at 60° C. for 20 hours, affording 29.2 g of the new Naltrexone HCl.

Figure 12:
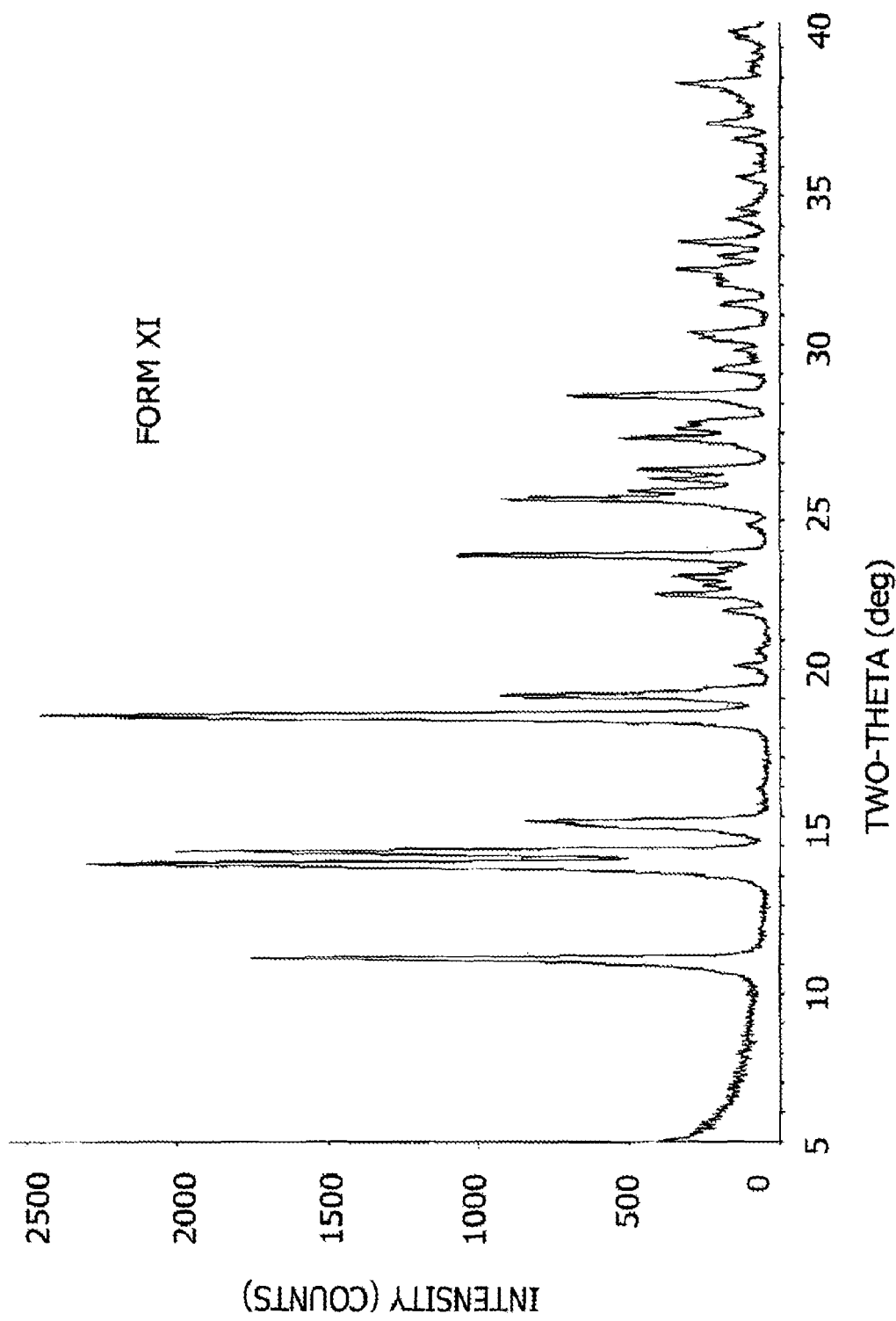
FIG. 12 shows the pXRD pattern for a new crystalline form of naltrexone hydrochloride—Form XI.

FIG. 12 shows the pXRD pattern for the crystalline form. Additionally, TGA analysis found that samples comprised of this particular crystalline form exhibited a small loss of mass below about 100° C. (e.g., between about 0.5 and about 2%, by mass).

While the present invention has been described for what are presently considered the preferred embodiments, the invention is not so limited. To the contrary, the invention is intended to cover various modifications and equivalent arrangements included within the spirit and scope of the detailed description provided above.

We claim:

1. A crystalline form of naltrexone hydrochloride hydrate selected from the group consisting of:
   (a) Form II having an x-ray diffraction pattern having characteristic peaks expressed in degrees 2θ (±0.2°) at 8.0, 10.8, 11.7, 12.9, 15.9, 17.1, 18.5, 20.8, 23.5, and 26.4;
   (b) Form VIII having an x-ray diffraction pattern having characteristic peaks expressed in degrees 2θ (±0.2°) at 11.4, 11.8, 13.1, 13.5, 15.9, 19.6, 22.6, 23.1, 24.5, and 25.8; and
   (c) Form XI having an x-ray diffraction pattern having characteristic peaks expressed in degrees 2θ (±0.2°) at 8.3, 11.5, 11.9, 16.5, 17.2, 21.9, 23.8, and 27.3.

Figure 2:
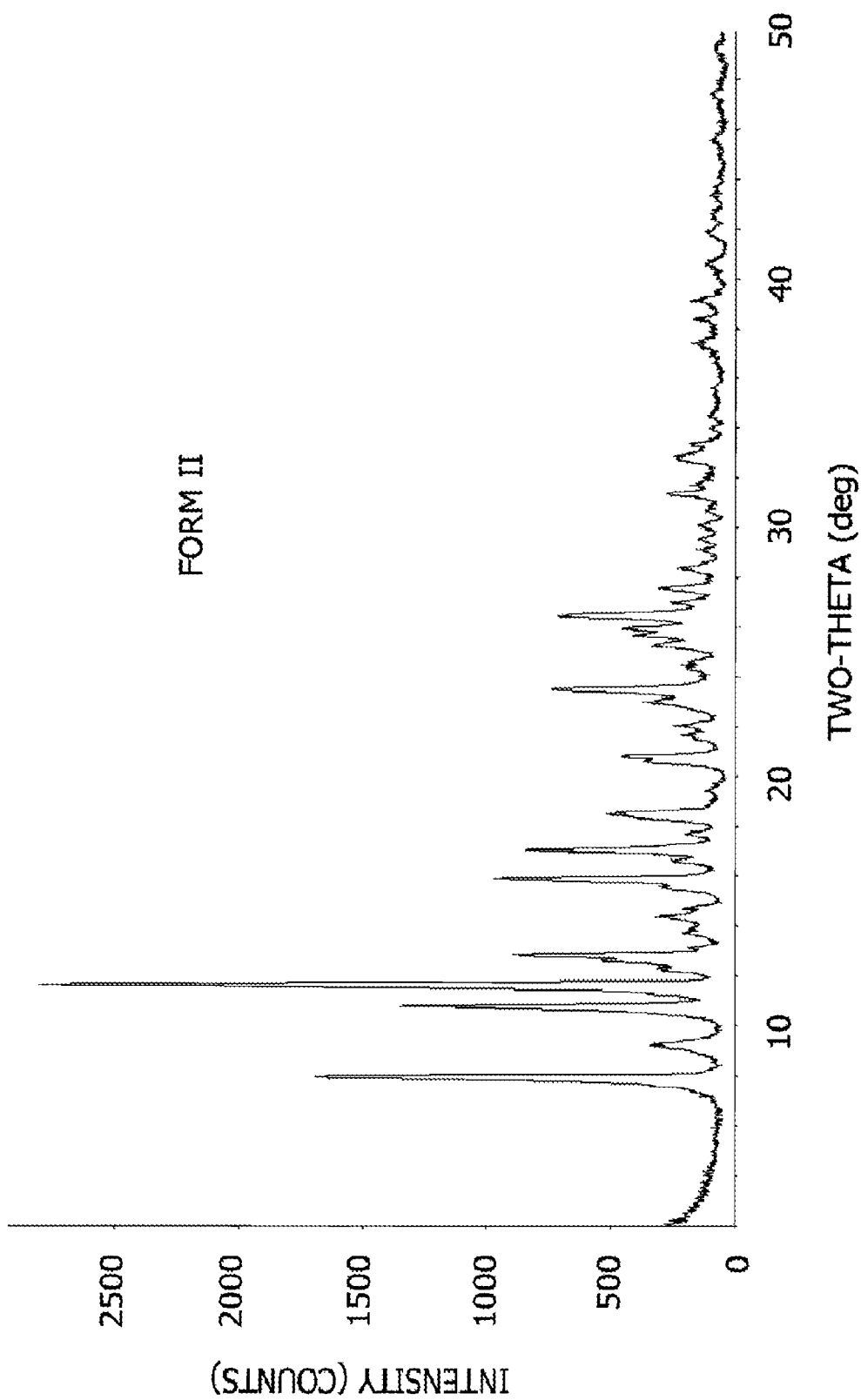
FIG. 2 shows the pXRD pattern for a new crystalline form of naltrexone hydrochloride—Form II.
Figure 3:
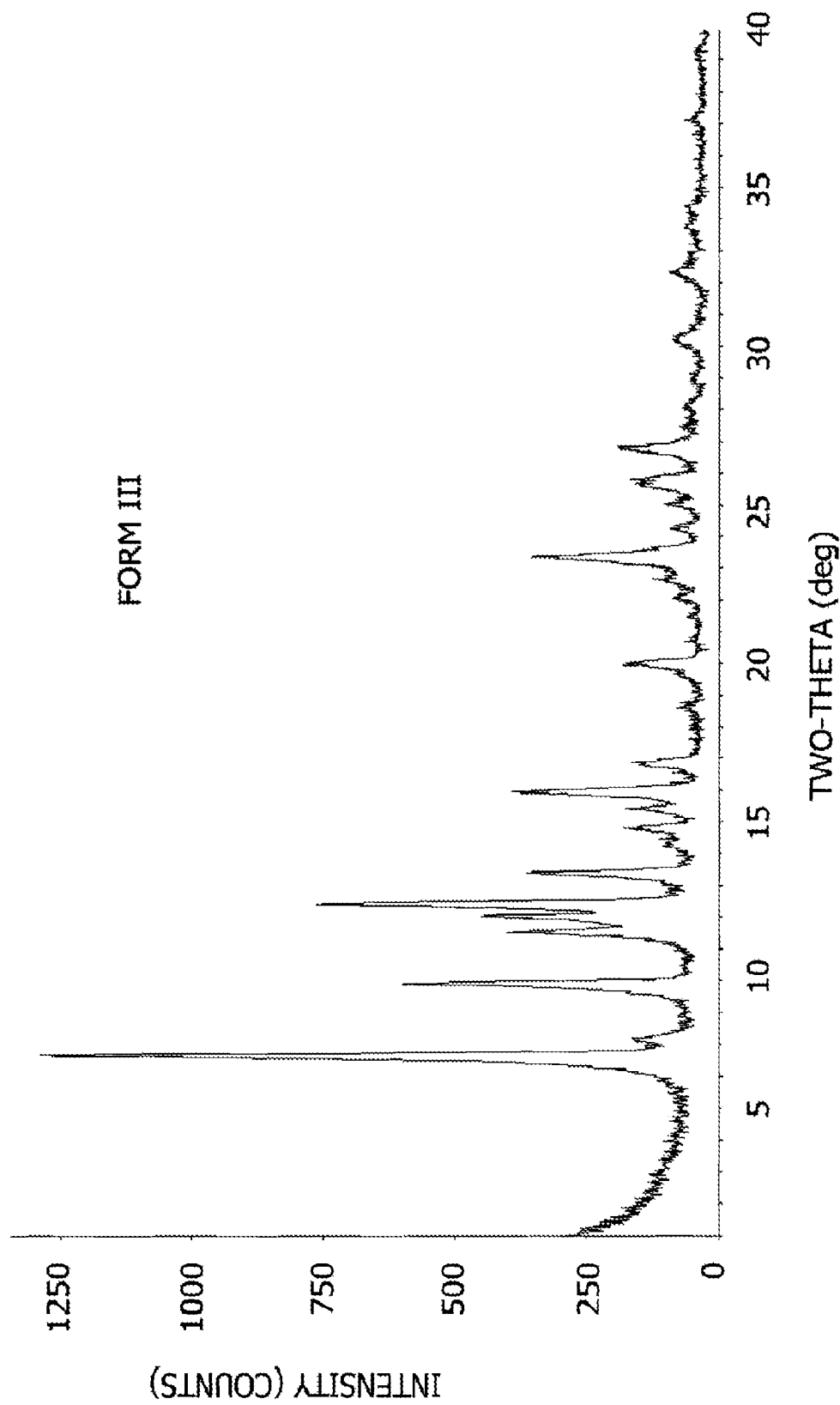
FIG. 3 shows the pXRD pattern for a new crystalline form of naltrexone hydrochloride—Form III.
Figure 4:
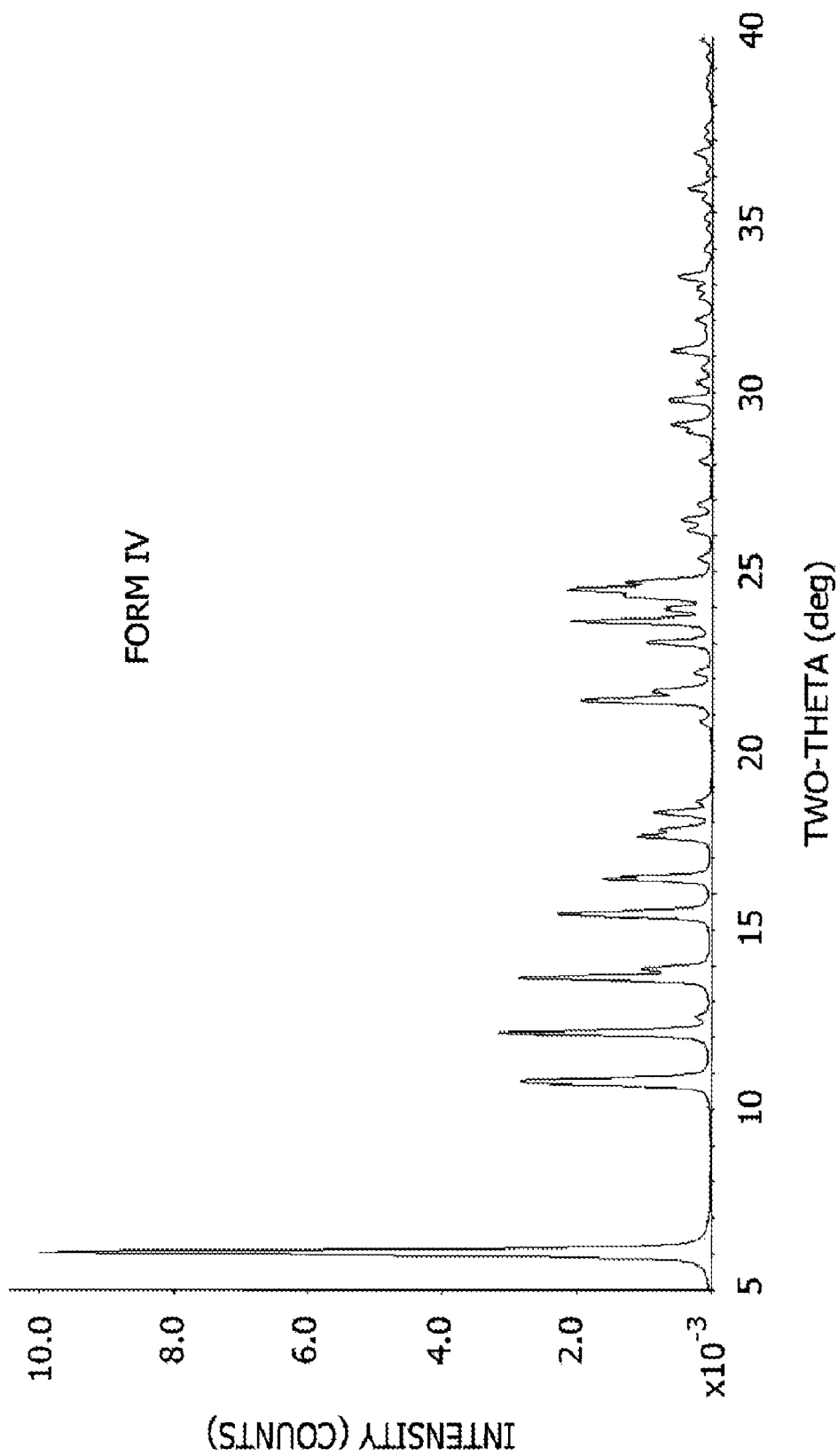
FIG. 4 shows the pXRD pattern for a new crystalline form of naltrexone hydrochloride—Form IV.
Figure 5:
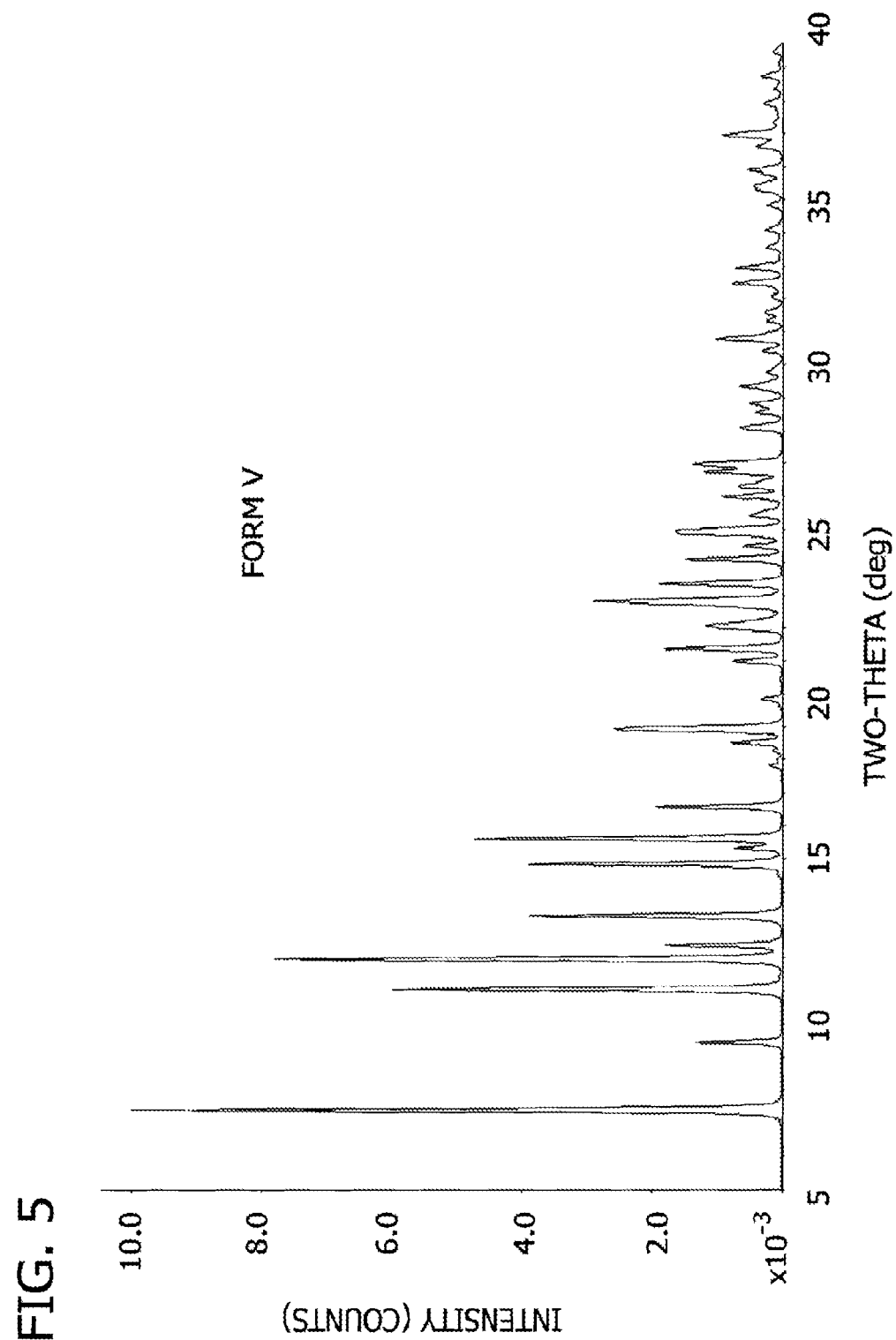
FIG. 5 shows the pXRD pattern for a new crystalline form of naltrexone hydrochloride—Form V.
Figure 6:
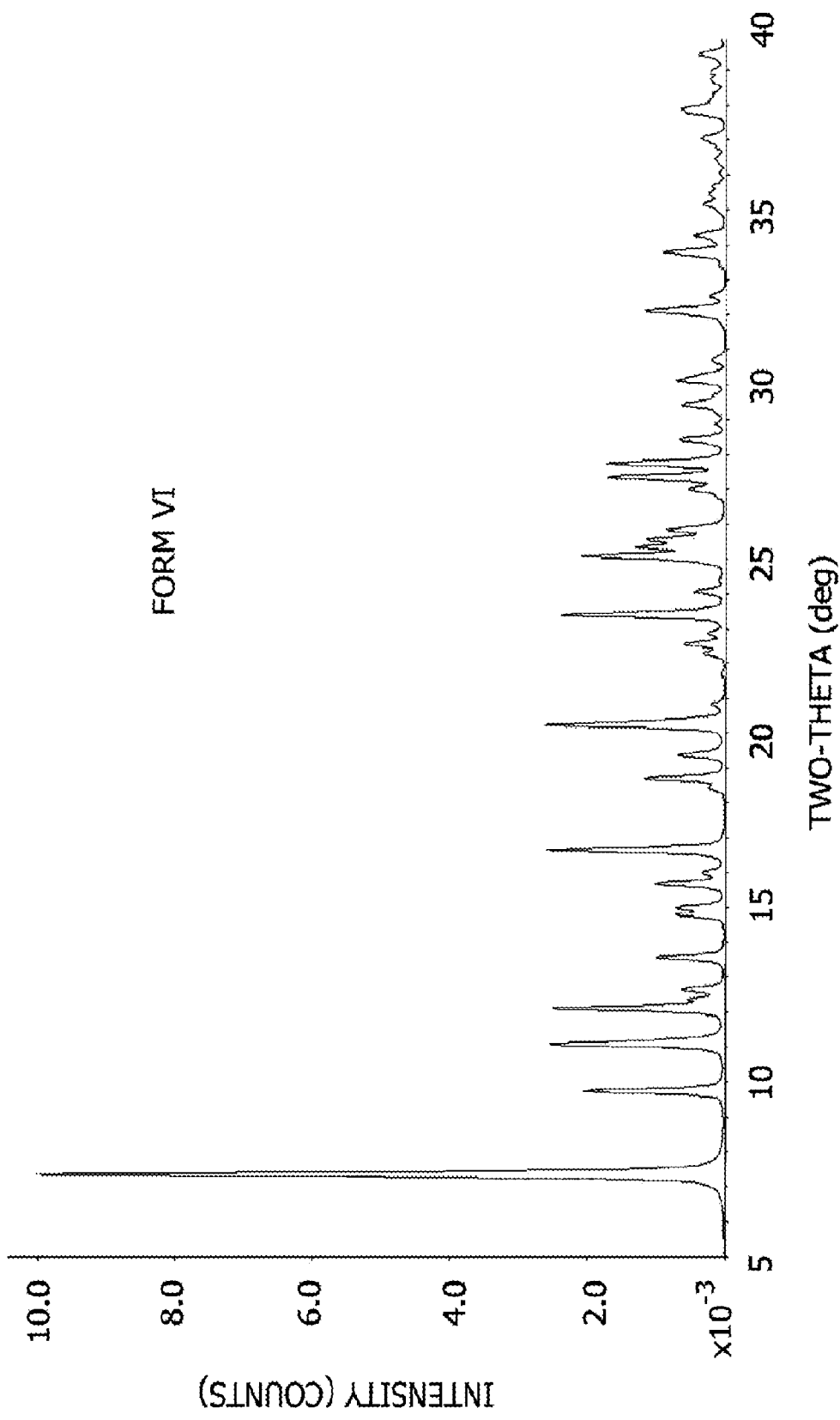
FIG. 6 shows the pXRD pattern for a prior art crystalline form of naltrexone hydrochloride tetrahydrate—Form VI.
Figure 7:
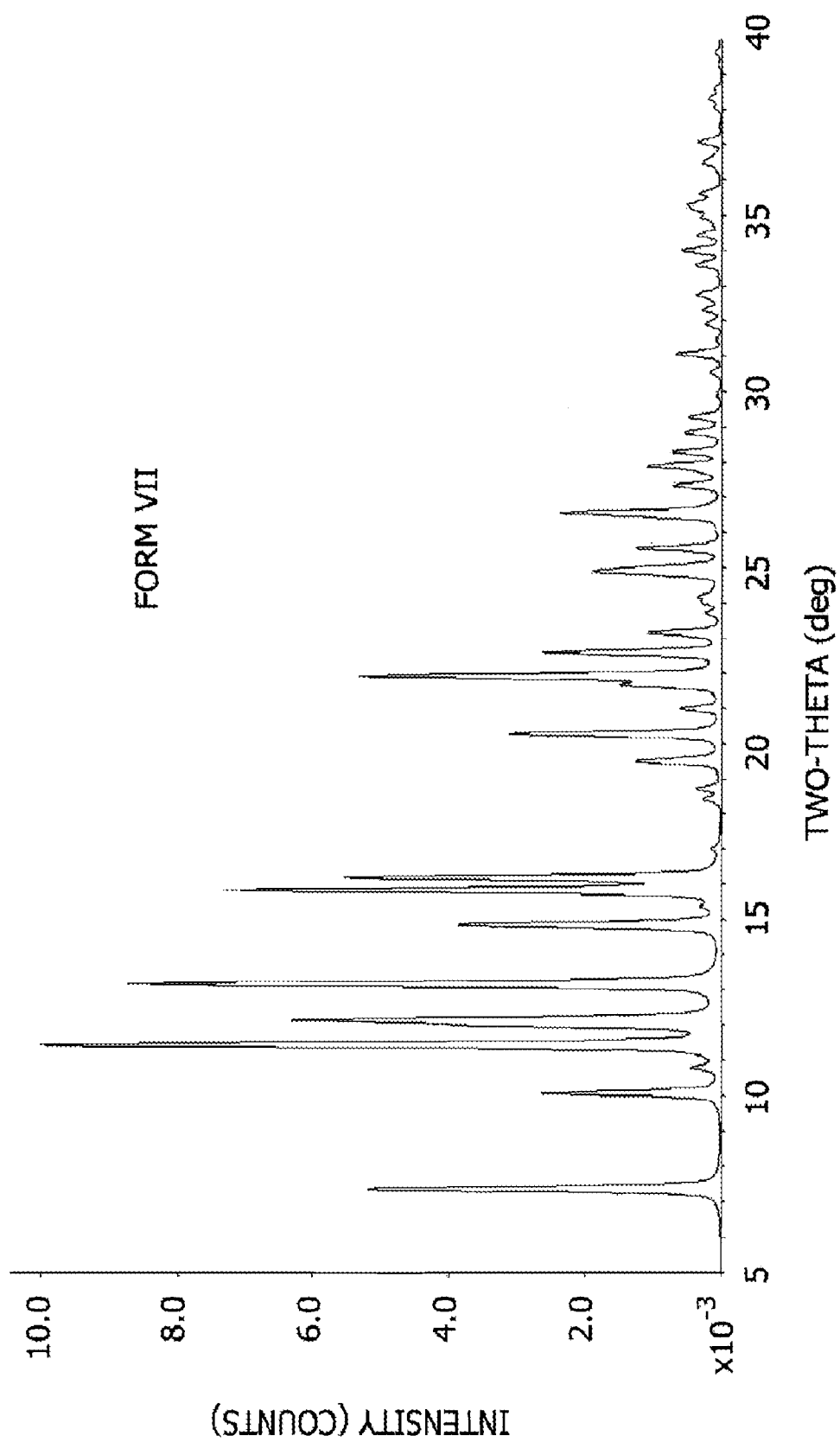
FIG. 7 shows the pXRD pattern for a new crystalline form of naltrexone hydrochloride—Form VII.

2. The crystalline form of naltrexone hydrochloride of claim 1(a), having a powder x-ray diffraction pattern substantially as shown in FIG. 2; wherein the crystalline form comprises bound water.

Figure 8:
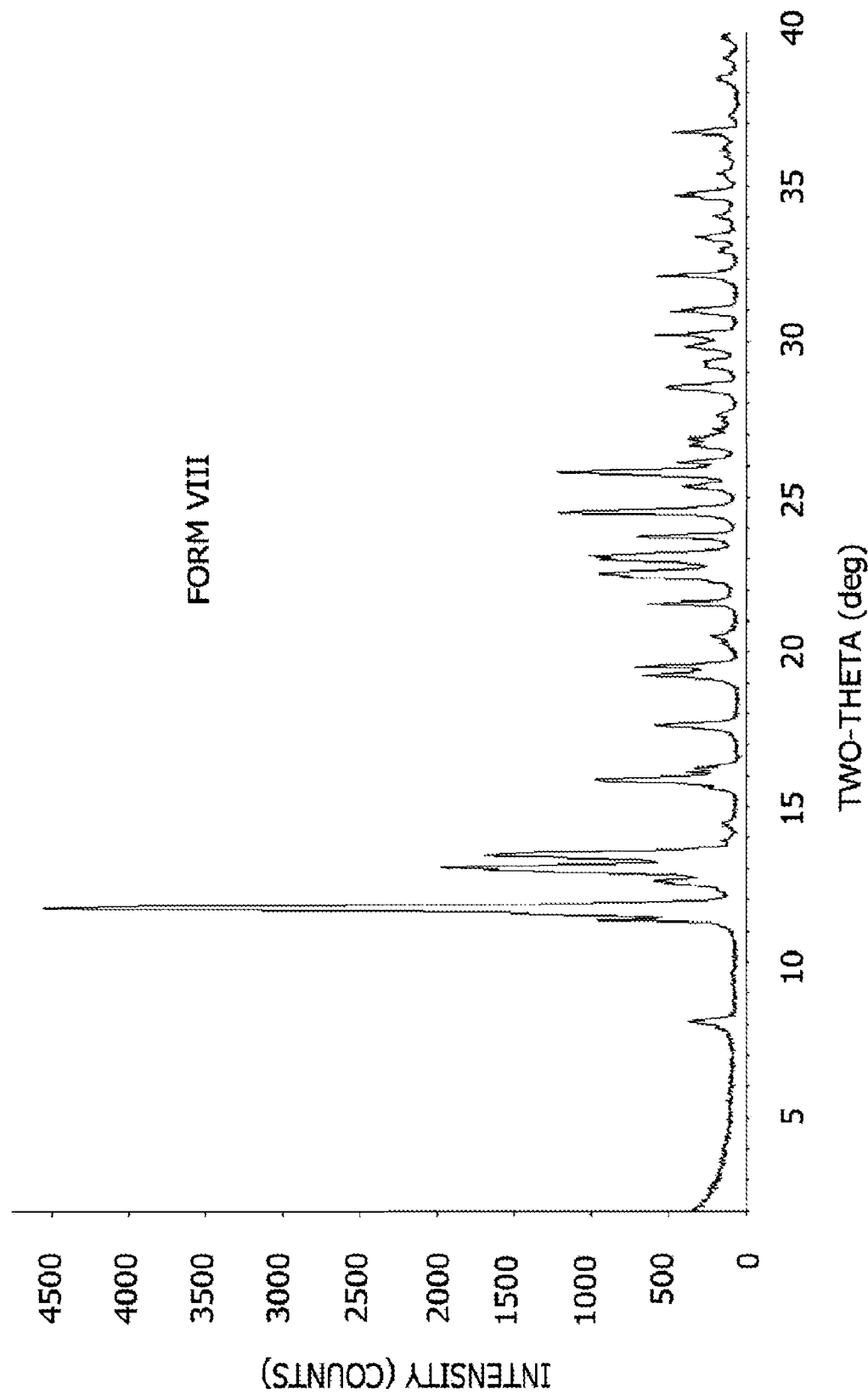
FIG. 8 shows the pXRD pattern for a new crystalline form of naltrexone hydrochloride—Form VIII.
Figure 9:
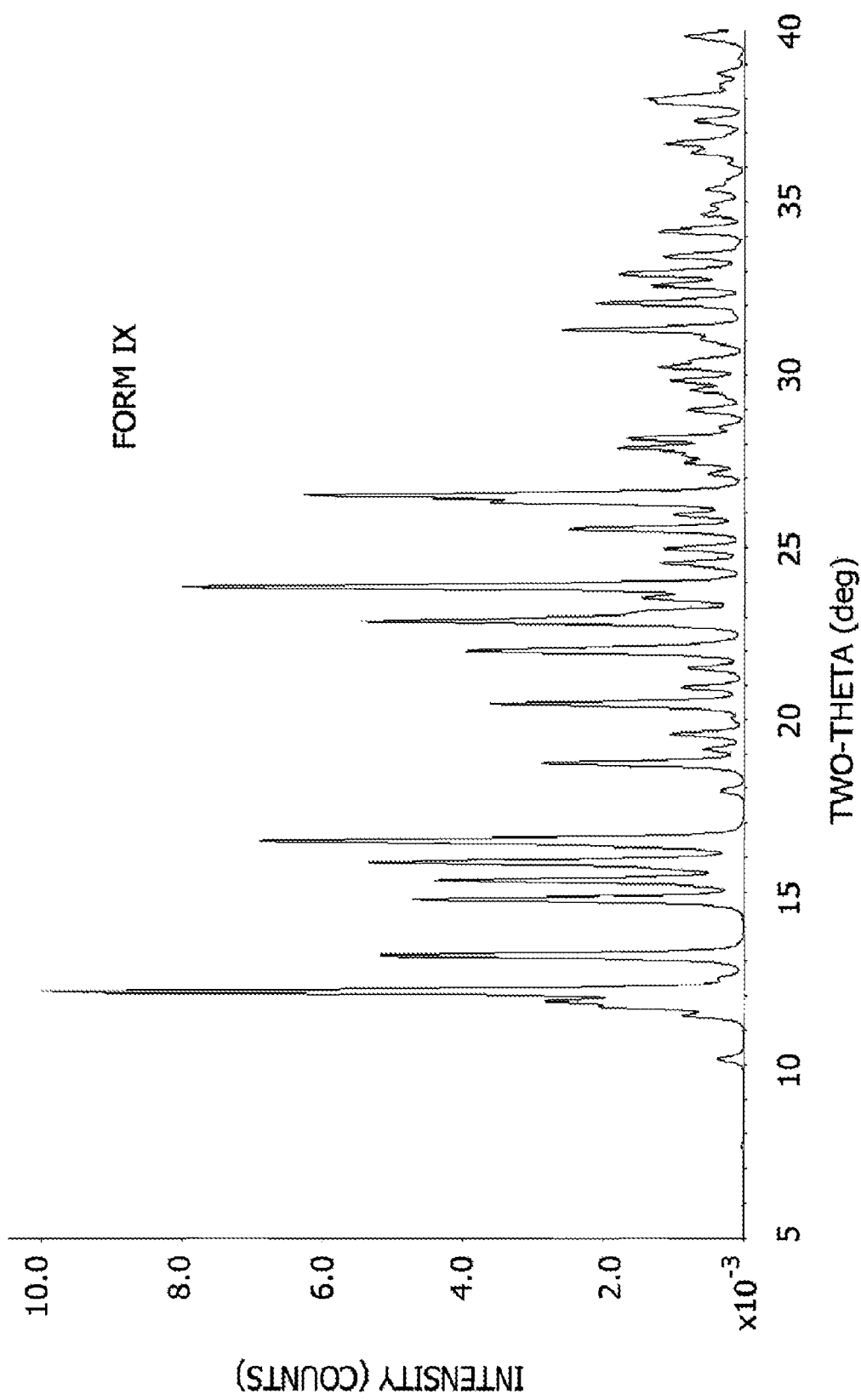
FIG. 9 shows the pXRD pattern for a new crystalline form of naltrexone hydrochloride—Form IX
Figure 10:
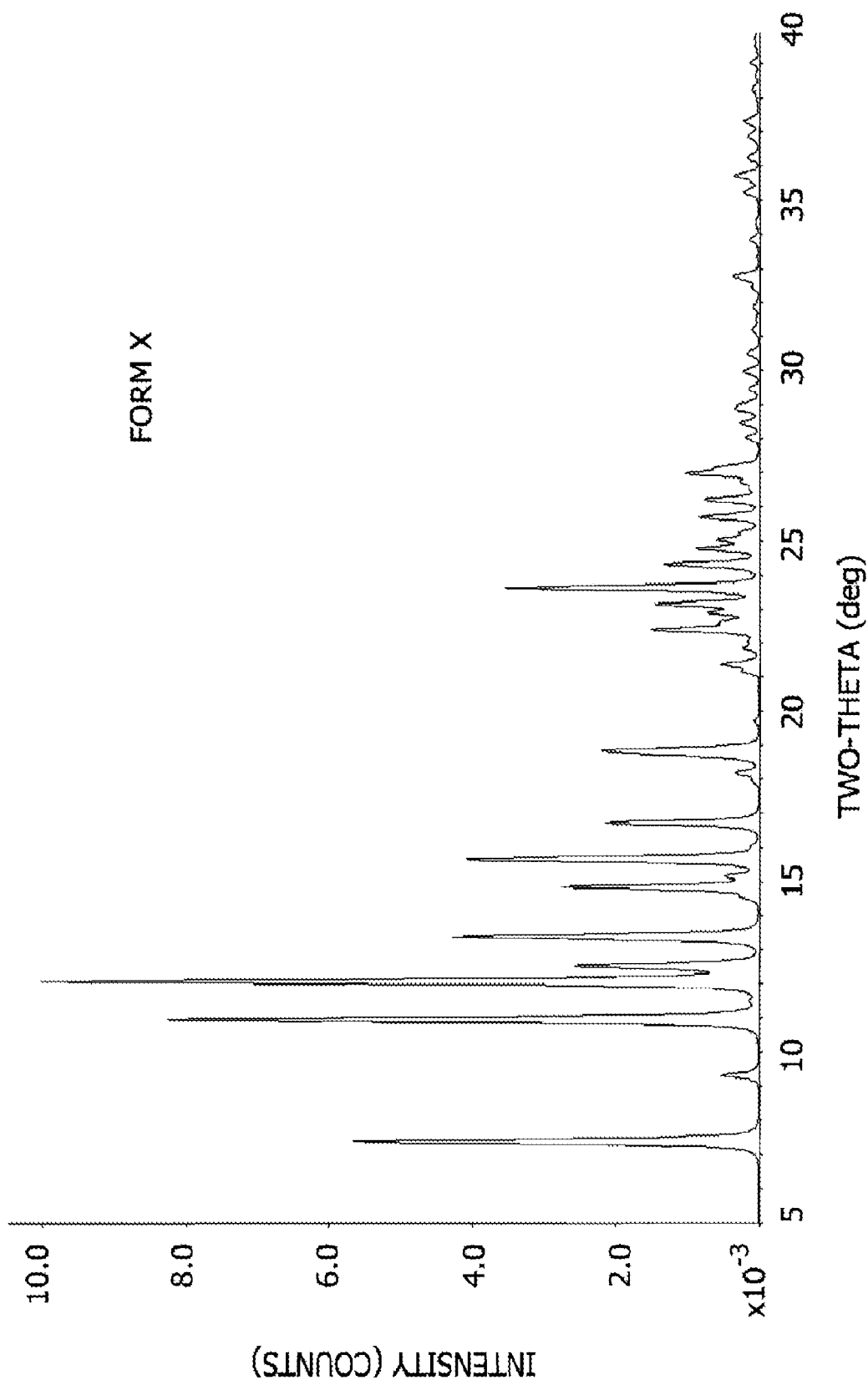
FIG. 10 shows the pXRD pattern for a new crystalline form of naltrexone hydrochloride—Form X.
Figure 11:
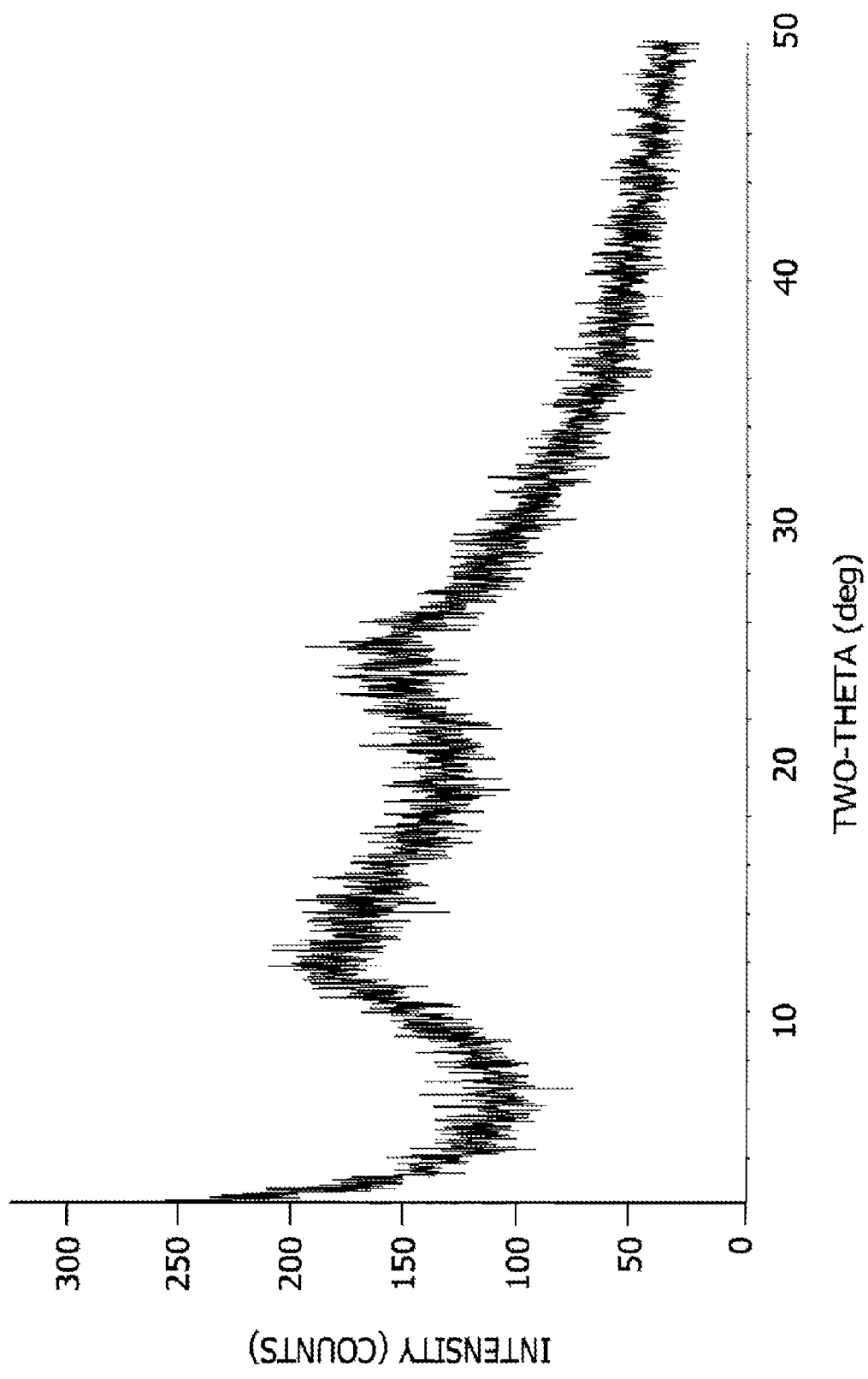
FIG. 11 shows the pXRD pattern for amorphous naltrexone hydrochloride.

3. The crystalline form of naltrexone hydrochloride of claim 1(b), having a powder x-ray diffraction pattern substantially as shown in FIG. 8; wherein the crystalline form comprises bound water.

4. The crystalline form of naltrexone hydrochloride of claim 1(c), having a powder x-ray diffraction pattern substantially as shown in FIG. 12; wherein the crystalline form comprises bound water.

5. A pharmaceutical composition comprising a therapeutically-effective amount of one or more of the naltrexone hydrochloride forms chosen from claim 1 and one or more pharmaceutically acceptable carriers, excipients or diluents thereof.

6. A method of treating alcohol dependence in a patient suffering therefrom, comprising the step of administering to said patient a therapeutically-effective amount of one or more of the naltrexone hydrochloride forms chosen from claim 1.

7. A method of making a crystalline form of naltrexone hydrochloride comprising: (i) adding an amount of naltrexone hydrochloride to a solvent system selected from the group consisting of methanol, isopropanol, ethanol, water, n-butanol, acetone, glacial acetic acid, ethyl acetate, methylene chloride, chloroform, acetonitrile, THF, hexane, toluene, DMSO, ethyl ether, and mixtures thereof, to create a nearly saturated solution; and (ii) evaporating the solvent system from the solution for an amount of time sufficient to induce crystallization of at least one crystalline form of naltrexone hydrochloride, wherein the crystalline form of naltrexone hydrochloride is selected from the forms set forth in claim 1.

8. A method of making a crystalline form of naltrexone hydrochloride comprising: (i) dissolving naltrexone hydrochloride in a first solvent system in a first container, wherein the first solvent system is selected from the group consisting of methanol and ethanol; (ii) adding a second solvent system to a second container, wherein the second solvent system is selected from the group consisting of ethyl acetate, hexane, chloroform, and ethyl ether, and wherein the second container is configured to receive the first container; and (iii) placing the first container in the second container for an amount of time sufficient to induce crystallization of at least one crystalline form of naltrexone hydrochloride, wherein the crystalline form of naltrexone hydrochloride is selected from the forms set forth in claim 1.

9. A method of converting a first crystalline form of naltrexone hydrochloride to a second crystalline form of naltrexone hydrochloride comprising: (i) adding an amount of the first crystalline form of naltrexone hydrochloride to a solvent system selected from the group consisting of methanol, isopropanol, ethanol, water, n-butanol, acetone, glacial acetic acid, ethyl acetate, methylene chloride, chloroform, acetonitrile, THF, hexane, toluene, DMSO, ethyl ether, and mixtures thereof to form a saturated solution; (ii) adding an additional amount of the first crystalline form of naltrexone hydrochloride to form a slurry; (iii) stirring the slurry for an amount of time sufficient to convert the first crystalline form of naltrexone hydrochloride to the second crystalline form of naltrexone hydrochloride; and (iv) filtering the solvent system from the slurry, wherein the second crystalline form of naltrexone hydrochloride is selected from the forms set forth in claim 1.

10. A method of making a crystalline form of naltrexone hydrochloride comprising: (I) forming a mixture comprising naltrexone hydrochloride and a solvent system selected from the group consisting of methanol, isopropanol, ethanol, water, n-butanol, acetone, glacial acetic acid, ethyl acetate, methylene chloride, chloroform, acetonitrile, THF, hexane, toluene, DMSO, ethyl ether, and mixtures thereof; (ii) heating the mixture; (iii) adding an amount of hydrochloric acid to the heated mixture; and (iv) cooling the resulting solution to induce crystallization of at least one crystalline form of naltrexone hydrochloride, wherein the crystalline form of naltrexone hydrochloride is selected from the forms set forth in claim 1.

* * * * *